(12) United States Patent
Cox (10) Patent No.: US 10,509,042 B2
(45) Date of Patent: Dec. 17, 2019

(54) IDENTIFICATION OF GLYCOSYLATION FORMS

(71) Applicant: DH Technologies Development PTE Ltd., Singapore (SG)

(72) Inventor: David Cox, North York (CA)

(73) Assignee: DH Technologies Development Pte. Ltd., Singapore (SG)

( * ) Notice: Subject to any disclaimer, the term of this patent is extended or adjusted under 35 U.S.C. 154(b) by 60 days.

(21) Appl. No.: 15/569,529

(22) PCT Filed: Apr. 25, 2016

(86) PCT No.: PCT/IB2016/052334
§ 371 (c)(1),
(2) Date: Oct. 26, 2017

(87) PCT Pub. No.: WO2016/174564
PCT Pub. Date: Nov. 3, 2016

(65) Prior Publication Data
US 2018/0299461 A1    Oct. 18, 2018

Related U.S. Application Data (60) Provisional application No. 62/155,132, filed on Apr. 30, 2015.

(51) Int. Cl.
| | | |
|---|---|---|
| G01N 33/68 | (2006.01) | |
| G01N 33/58 | (2006.01) | |
| G01N 30/72 | (2006.01) | |
| C12Q 1/34 | (2006.01) | |

(52) U.S. Cl.
CPC .......... G01N 33/6842 (2013.01); C12Q 1/34 (2013.01); G01N 30/72 (2013.01); G01N 33/58 (2013.01); G01N 33/6848 (2013.01); G01N 2333/924 (2013.01); G01N 2400/10 (2013.01); Y10T 436/143333 (2015.01); Y10T 436/24 (2015.01)

(58) Field of Classification Search
CPC .............. C12Q 1/34; G01N 2333/914; G01N 2333/924; G01N 2400/10; G01N 30/72; G01N 33/58; G01N 33/68; G01N 33/6842; G01N 33/6848; Y10T 436/13; Y10T 436/24; Y10T 436/143333
USPC ............... 436/56, 86, 87, 161, 173, 512, 94; 435/18, 23, 24
See application file for complete search history.

(56) References Cited

U.S. PATENT DOCUMENTS

| | | | | |
|---|---|---|---|---|
| 2006/0057638 A1* | 3/2006 | Bosques | ............ | G01N 33/6803 435/7.1 |
| 2007/0259398 A1* | 11/2007 | Arnott | ..................... | C12P 21/00 435/68.1 |
| 2007/0269895 A1 | 11/2007 | Aebersold et al. | | |
| 2009/0053828 A1 | 2/2009 | Regnier et al. | | |
| 2011/0213137 A1* | 9/2011 | Bosques | ............... | C07B 59/005 536/55.3 |
| 2013/0171658 A1* | 7/2013 | Fulton | ..................... | C08B 37/00 435/7.1 |

OTHER PUBLICATIONS

Zhang et al. Talanta, vol. 91, Jan. 21, 2012, pp. 122-127.*
Cao et al. Journal of Proteome Research, vol. 13, Feb. 14, 2014, pp. 1485-1493.*
Shetty et al. Analytical Chemistry, vol. 82, No. 22, Nov. 15, 2010, pp. 9201-9210.*
Shetty et al. Clinical Proteomics, vol. 9:10, Sep. 1, 2010, pp. 1-19.*
Ueda et al. Molecular and Cellular Proteomics, vol. 9.9, Jun. 21, 2010, pp. 1819-1828.*
International Search Report and Written Opinion for PCT/IB2016/052334 dated Jul. 22, 2016.
Liu et al., 'Mass spectrometry-based analysis of glycoproteins and its clinical applications in cancer biomarker discovery' Clinical Proteomics, vol. 11, Article 14, pp. 1-9 (2014) See the whole document.
Roth et al., 'Identification and quantification of protein glycosylation' International Journal of Carbohydrate Chemistry, vol. 2012, Article 640923, pp. 1-10 (2012) See the whole document.
Zhang, et al., 'Mass spectrometry-based N-glycoproteomics for cancer biomarker discovery' Clinical Proteomics, vol. 11, Article 18, pp. 1-14, (2014). See the whole document.
Vivekananda Shetty et al: "Investigation of ovarian cancer associated sialylation changes in N-linked glycopeptides by quantitative proteomics", Clinical Proteomics, Biomed Central Ltd, London, UK, vol. 9, No. 1, Aug. 2, 2012, p. 10.
Thaysen-Andersen Morten et al: "Advances in LC-MS/MS-based glycoproteomics: Getting closer to system-site-specific mapping of the N- and O-glycoproteome", Biochimica Et Biophysica Acta, vol. 1844, May 12, 2014, pp. 1437-1452.
Sheng Pan et al: "Mass Spectrometry Based Glycoproteomics—From a Proteomics Perspective", Molecular & Cellular Proteomics, vol. 10.1, Aug. 27, 2010 pp. 1-14.

* cited by examiner

Primary Examiner — Maureen Wallenhorst (57) ABSTRACT

The present teachings relate to methods, systems, and kits for analyzing a sample containing a glycopeptide of interest that can subject the glycopeptide of interest to a plurality of parallel deglycosylation reactions that differentially cleave the glycan, with the various products resulting from the deglycosylation reactions being differentially labeled (e.g., with isobaric and/or isomeric labeling reagents) to thereby produce labeled glycopeptides or labeled fragments of the glycopeptides. The products of the various deglycosylation reactions can then be mixed together and subject to LC-MS/MS using a single injection of the mixture. In accordance with various aspects, by associating the resulting mass spectral data with a particular deglycosylation reaction (e.g., based on the presence in the MS/MS data of product reporter ions associated with the particular differential labels), the methods and systems described herein can aid in the identification of the glycan structure.

4 Claims, 4 Drawing Sheets

IDENTIFICATION OF GLYCOSYLATION FORMS

RELATED APPLICATIONS

This application claims the benefit of priority from U.S. Provisional Application Ser. No. 62/155,132, filed on Apr. 30, 2015, the entire contents of which is incorporated by reference herein.

FIELD

The present teachings generally relate to methods, systems, and kits for the mass spectrometric analysis of a sample, and more particularly, for the analysis of glycopeptides.

INTRODUCTION

Protein glycosylation typically refers to a post-translational modification in which an oligosaccharide or glycan is attached to a protein. Given the importance of glycosylation on protein folding, transport, and cell-cell interactions, for example, many research tools have been developed to characterize and/or analyze glycopeptides and the glycans associated therewith. Such tools have become critical in the biomedical sciences, biopharmaceutical industry (e.g., biomarker discovery), and in efficacy/safety assessment of protein therapeutics for regulatory agencies.

Though known mass spectrometry-based methods can be effective in determining the location and/or structure of the glycans associated with the glycopeptides, these methods can necessitate extensive complex, multi-step mass spectrometric analysis (e.g., with multiple sample injections) and require a high-level of skill in interpreting the resulting mass spectra.

Accordingly, there remains a need for efficient and effective methods for the analysis of glycopeptides and/or the identification of their glycans.

SUMMARY

In accordance with various aspects of the applicant's teachings, methods of analyzing a sample containing (or suspected of containing) a plurality of a glycopeptide of interest (a glycan bonded to a peptide, e.g., a glycoprotein, an antibody) are provided. In certain aspects, the method can comprise separately reacting the sample with a plurality of glycosidases, each of which is effective to cleave a different glycosidic bond. Products of each of the separate (e.g., parallel) reactions between the glycopeptide and the particular glycosidase can then be differentially labeled, mixed together, and subject to liquid chromatography-tandem mass spectrometry (LC-MS/MS). Rather than a typical multi-step analysis in which the glycopeptide of interest is iteratively exposed to particular glycosidases with the products from each reaction being separately injected into the MS in a complex and time-consuming protocol, methods and systems in accordance with the present teachings can enable a single sample injection into the LC-MS/MS, with the differential labels indicating the particular reaction of the glycopeptide with the respective glycosidase and the identity and/or quantity of the sugars cleaved by this reaction. By using a single LC-MS/MS run to analyze the results across the plurality of reactions to which the glycopeptide of interest is subjected, methods in accordance with various aspects of the present teachings can provide for increased throughput and decreased complexity and variability (e.g., between runs), while also making the identification of glycosylation forms more easily subject to automation relative to traditional techniques. In some aspects, the methods and systems described herein can subject a glycopeptide of interest to an array of various glycosidases so as to generate a deglycosylation signature for the array, which can be compared to the deglycosylation profile of known or predicted glycopeptides so as to positively identify aspects of the glycan structure and/or to eliminate possible glycan structures from further consideration.

In accordance with various aspects of the present teachings, a method of analyzing glycopeptides is provided that comprises reacting, in a first reaction, a first portion of a sample containing a glycopeptide of interest (i.e., a glycan bonded to a peptide) with a first labeling reagent, wherein a product of the first reaction comprises a labeled glycopeptide; reacting, in a second reaction, a second portion of the sample containing said glycopeptide with a first glycosidase and a second labeling reagent different from the first labeling reagent, wherein the reaction with the first glycosidase is effective to release the glycan from the peptide, and wherein a product of the second reaction is a labeled peptide; and reacting, in a third reaction, a third portion of the sample containing said glycopeptide with a second glycosidase different from the first glycosidsase and a third labeling reagent different from the first and second labeling reagents, wherein the reaction with the second glycosidase is effective to cleave a portion of the glycan from the glycopeptide so as to form a cleaved glycan portion and a cleaved glycopeptide comprising a non-cleaved glycan portion bonded to the peptide, and wherein a product of the third reaction is a labeled, cleaved glycopeptide. Products of the first, second, and third reactions can be combined so as to form a mixture containing the labeled glycopeptide, the labeled peptide, and the labeled, cleaved glycopeptide, if any, and liquid chromatography-mass spectrometry can then be performed on the mixture. In various aspects, the first, second, and third labeling reagents can comprise iTRAQ labels. In various aspects, in the second reaction, the reaction with the second labeling reagent can occur before, during, or after the glycopeptide is reacted with the first glycosidase, and in the third reaction, the reaction with the third labeling reagent can occur before, during, or after the glycopeptide is reacted with the second glycosidase.

In some aspects, for example, the step of performing liquid chromatography-mass spectrometry on the mixture can comprise applying the mixture to a liquid chromatography column in a single injection and comparing the mass spectra at different elution times to determine a mass of one or more of the glycopeptide, the peptide, and the cleaved glycopeptide. In some related aspects, the method can further comprise one or more of i) determining a mass of the glycan based on a difference between a mass of the glycopeptide and a mass of the cleaved glycopeptide, ii) determining a mass of the non-cleaved glycan portion based on a difference between a mass of the cleaved glycopeptide and a mass of the peptide, and iii) determining a mass of the cleaved glycan portion based on a difference between a mass of the glycopeptide and a mass of the cleaved glycopeptide.

Additional reactions of the sample with other glycosidases can also be utilized in accordance with the present teachings. By way of example, in some aspects, the reaction with the second glycosidase (i.e., the third reaction referenced above) can form a first cleaved glycan portion and a first cleaved glycopeptide comprising a non-cleaved glycan portion bonded to the peptide, and the method can further comprise reacting, in a fourth reaction, a fourth portion of the sample with a third glycosidase different from the first and second glycosidases, the third glycosidase configured to cleave the glycan so as to form a second cleaved glycan portion and a second cleaved glycopeptide comprising a second non-cleaved glycan portion bonded to the peptide. The second cleaved glycopeptide can also be labeled with a fourth labeling reagent so as to form a second labeled cleaved glycopeptide, wherein the fourth labeling reagent is different from the first, second, and third labeling reagents. The products of the fourth reaction can then be mixed with the products of said first, second, and third reactions prior to performing liquid chromatography-mass spectrometry on the mixture. In various related aspects, the method can further comprise determining a mass of one or more of the first cleaved glycan portion, the first non-cleaved glycan portion, the second cleaved glycan portion, and the second non-cleaved glycan portion based on mass spectra data generated by the liquid chromatography-mass spectrometry.

It will be appreciated that a variety of glycosidases can be used in accordance with the present teachings. For example, in various aspects, the first glycosidase can comprise PNGase and the second glycosidase can comprise an endoglycosidase. Non-limiting examples of glycosidases suitable for use in accordance with the present teachings include PNGase, endoglycosidases (e.g., Endoglycosidase H, Endoglycosidase F, Endo-β-galactosidase) and exoglycosidases (e.g., N-acetylglucosaminidase, fucosidase, galactosidase, glucosidase, mannosidase, neuraminidase, and xylosidase), and mixtures thereof.

In accordance with various aspects of the present teachings, a method of analyzing a sample is provided that comprises separately reacting a sample with a plurality of glycosidases each of which is effective to cleave a different glycosidic bond (e.g., to form a cleaved glycan portion and a cleaved glycopeptide comprising a non-cleaved glycan portion bonded to the peptide), the sample containing a plurality of a glycopeptide of interest; differentially labeling products of each reaction between the glycopeptide and the glycosidase; mixing the differentially labeled glycopeptide products; and performing liquid chromatography-mass spectrometry on the mixture of differentially labeled glycopeptide products.

In various aspects, the method can further comprise determining if a cleaved glycan portion resulted from the reaction of the glycopeptide with each of the plurality of glycosidases. In some related aspects, the method can further comprise at least partially determining a structure of the glycan based on the determination of whether a cleaved glycan portion resulted from the reaction of the glycopeptide with each of the plurality of glycosidases. Additionally or alternatively, the method can also comprise at least one of comparing a mass of the cleaved glycan portions with known glycan structures to at least partially determine the structure of the glycan and/or comparing a mass of non-cleaved glycan portions remaining bonded to the peptide resulting from each reaction with known glycan structures to at least partially determine the structure of the glycan.

In some aspects of the present teachings, methods and systems provided herein can enable eluate being transferred from a liquid chromatograph to a mass spectrometer to be split into one or more fluid streams such that a portion of the eluate can be additionally reacted with a glycosidase during transfer. In one aspect, the glycosidase for reacting with one of the fluid streams can be effective to remove the glycan from the glycopeptide, e.g., by cleaving an asparagine-linked glycan from a fraction of differentially labeled glycopeptide products present in the eluate. Because the compounds in the eluate entering the split flow are eluted at the same elution time, at any given elution time of the differentially labeled glycopeptide products, the mass spectra can exhibit a peak corresponding to the mass of the glycopeptide product at that elution time and a peak corresponding to the mass of the bare peptide (i.e., after the glycan is removed via the additional reaction of the glycopeptide product with the glycosidase in the split fluid flow paths). In various aspects, the glycosidase reacted with the eluate can comprise PNGase, while in some aspects, one of the plurality of glycosidases separately reacted with the sample can also comprise PNGase.

In various aspects, the methods can also comprise determining the presence of cleaved glycan portions, if any, resulting from each of the reactions of the glycopeptide with the plurality of glycosidases, and optionally, comparing a mass of the cleaved glycan portions with known glycan structures to at least partially determine the structure of the glycan.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

It will be appreciated that for clarity, the following discussion will explicate various aspects of embodiments of the applicants' teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicants' teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicants' teachings in any manner.

In accordance with various aspects of the present teachings, the methods, systems, and kits described herein for analyzing a sample containing a glycopeptide of interest can enable increased throughput, decreased complexity, and decreased intra-run variability, while also facilitating automated analysis of the identification of glycosylation forms.

Whereas the determination of glycan structures using conventional techniques typically requires a high level of user skill and multi-step procedures that iteratively expose a glycan of interest to selected glycosidases, with the products from each reaction being separately subject to MS/MS analysis, methods and systems in accordance with the present teachings can subject the glycopeptide of interest to a plurality of parallel deglycosylation reactions that differentially cleave the glycan, with the various products resulting from the deglycosylation reactions being differentially labeled (e.g., with isobaric and/or isomeric labeling reagents) to thereby produce labeled glycopeptides or labeled fragments of the glycopeptides. The products of the various deglycosylation reactions can then be mixed together and subject to LC-MS/MS using a single injection of the mixture. In accordance with various aspects, by associating the resulting mass spectral data with a particular deglycosylation reaction (e.g., based on the presence in the MS/MS data of product reporter ions associated with the particular differential labels), the methods and systems described herein can aid in the identification of the glycan structure. By way of non-limiting example, by subjecting a glycopeptide of interest to an array of various glycosidases, a deglycosylation signature (e.g., specific to the array) can be determined that can be compared to known glycan structures so as to positively identify aspects of the glycan and/or to eliminate possible structures from further consideration.

Figure 1:
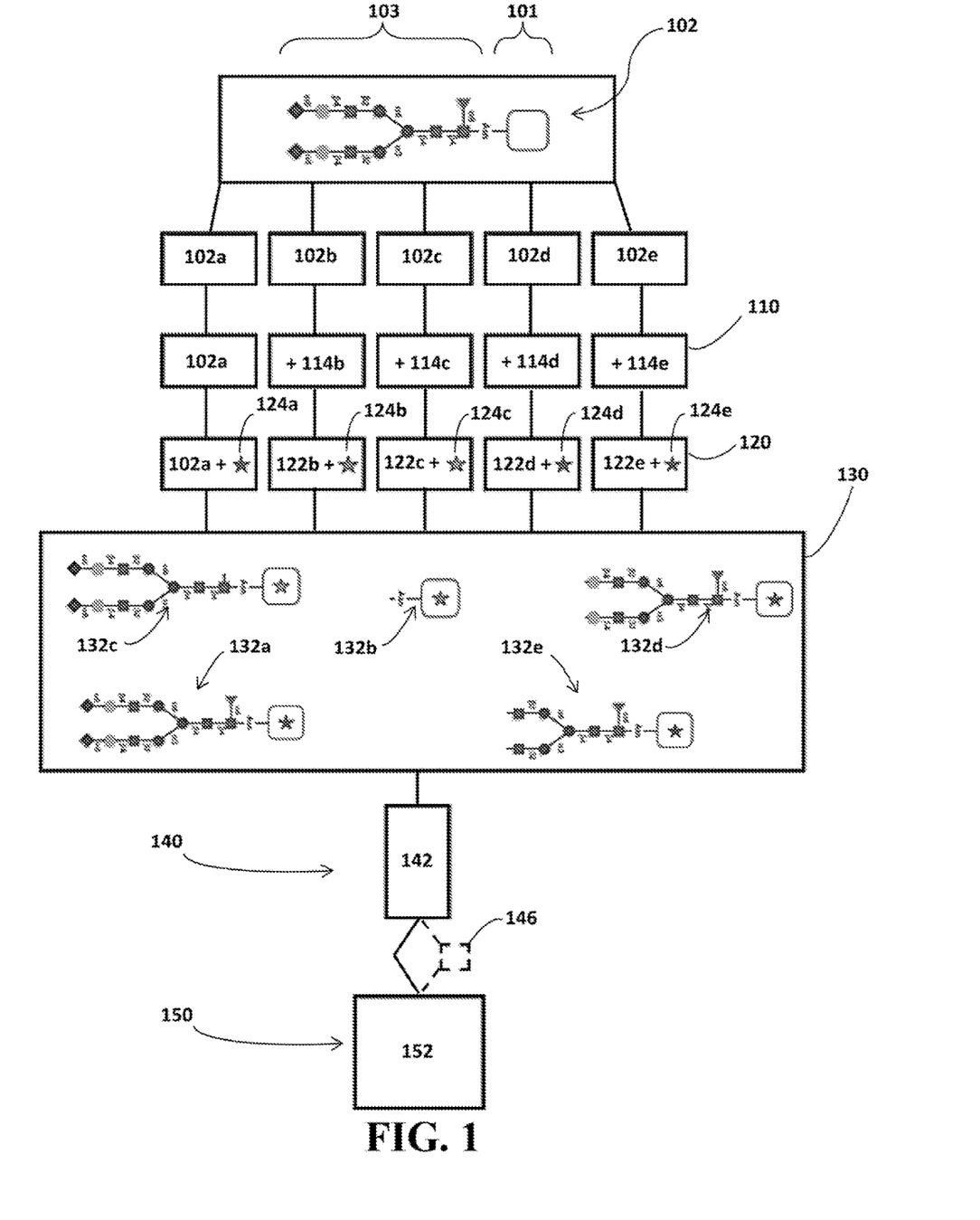
FIG. 1 illustrates an exemplary workflow for analyzing a sample containing a glycopeptide of interest in accordance with various aspects of the applicant's teachings.

With reference now to FIG. 1, an exemplary method of analyzing glycopeptides in accordance with various aspects of the present teachings will now be described. According to the illustration of FIG. 1, a sample comprising a glycopeptide of interest 102 (e.g., glycan 103 bonded to peptide 101 at an amide nitrogen of an asparagine (Asn) residue of a protein) can be separated into a plurality of sample portions 102a-e (e.g., aliquots, an array of sample wells in a 96-well plate), each of which contains the glycopeptide 102. In step 110, one or more glycosidases 114b-e can be added to each sample portion 102b-e, while no glycosidase is added to sample portion 102a. Because each glycosidase 114b-e can be effective to cleave a particular glycosidic bond as discussed elsewhere herein, the reactions of the sample portions 102b-e with the particular glycosidases 114b-e can result in a specific deglycosylation product 122b-e. By way of example, if the glycosidic bond for which the particular glycosidase 114b-e is effective is present within the glycopeptide 102, reaction of each glycosidase 114b-e with the sample portion 102b-e can be effective to cleave a different portion of the glycan 103 from the glycopeptide 102, thereby resulting in a cleaved glycopeptide 122b-e (i.e., the bare peptide 101 with a non-cleaved portion of the glycan 103 still attached) and a cleaved glycan portion (i.e., the portion of the glycan 103 that is cleaved from the glycopeptide 102). In step 120 in the exemplary depicted method of FIG. 1, a labeling reaction can then be performed such that a different label 124a-e (e.g., iTRAQ 114 as labeling reagent 124a, iTRAQ 115 as labeling reagent 124b, iTRAQ 116 as labeling reagent 124c, iTRAQ 117 as labeling reagent 124d, iTRAQ 118 as labeling reagent 124e, etc.) is added to each of the sample portion 102a and the deglycosylation products 122b-e, if any, resulting from the various reactions in step 110. Though step 120 depicts adding a differential label 124a-e after the deglycosylation reactions in step 110, it should be appreciated that the differential labeling reagents 124a-e can be added before, during, or after the formation of the deglycosylation products 122b-e (e.g., the glycopeptide 102 in the various sample portions 102a-e can be differentially labeled before or during the deglycosylation reactions in step 110). The various labeled products 132a-e can then be mixed together in step 130 for injection into an LC 142 in step 140, with the eluate from the LC 142 being transferred to the mass spectrometer 152 for analysis (e.g., MS/MS) in the step 150. As discussed in detail below with reference to FIG. 2, the detection of a specific differential reporter ion from labels 124a-e dissociated from each of the labeled products 132a-e in MS/MS mode can then be used to determine the specific reaction in step 110 corresponding to the MS or MS/MS spectra at a given elution time from the LC 142. Furthermore, in accordance with various aspects of the present teachings, the generated MS spectra at different elution times can be compared to indicate the mass, identity, and/or structure of the glycan 103 bonded to the glycan 101 in the glycopeptide 102.

Figure 2:
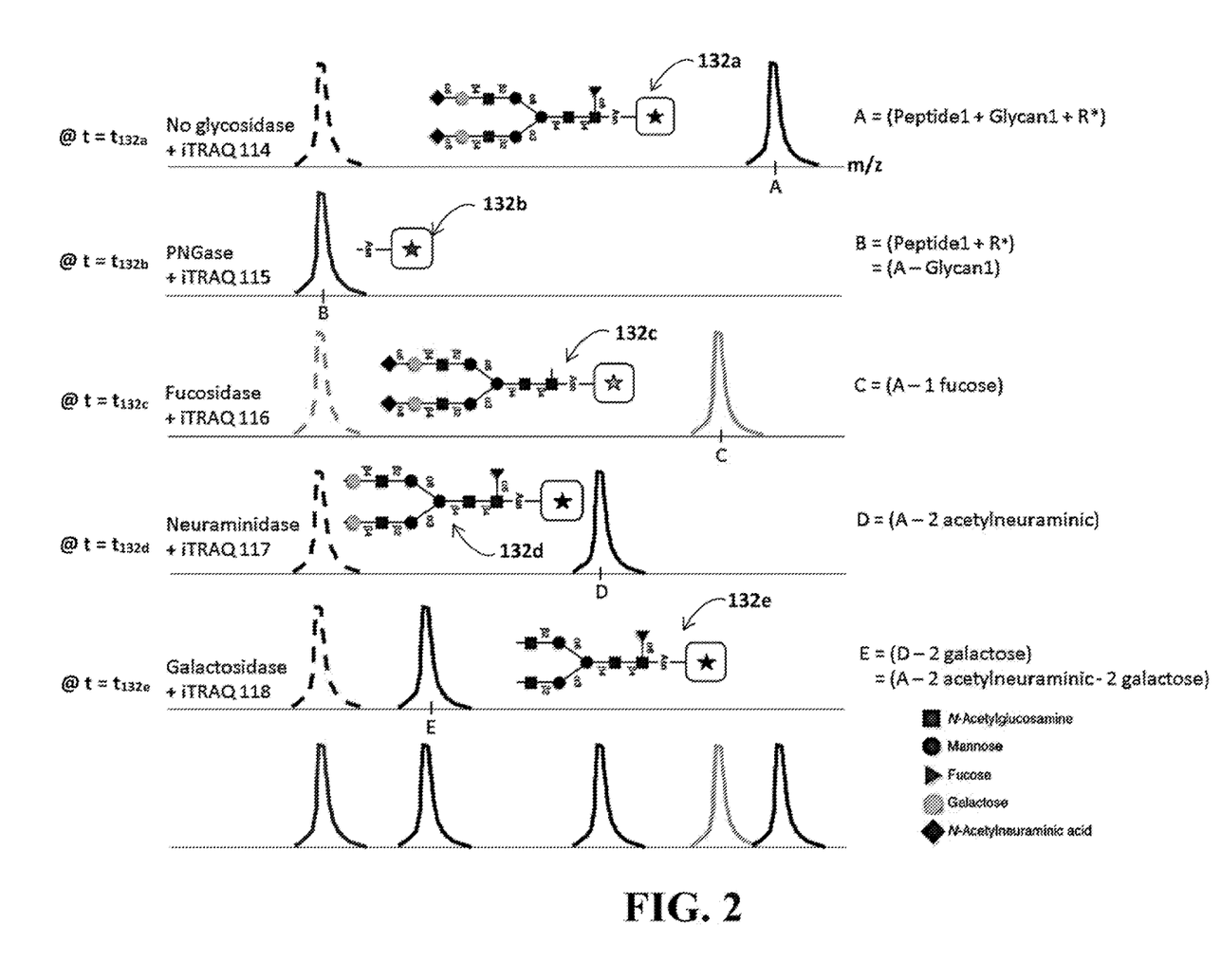
FIG. 2 illustrates exemplary mass spectra resulting from a glycopeptide subject to multiple deglycosylation reactions in the exemplary workflow depicted in FIG. 1.
Figure 4:
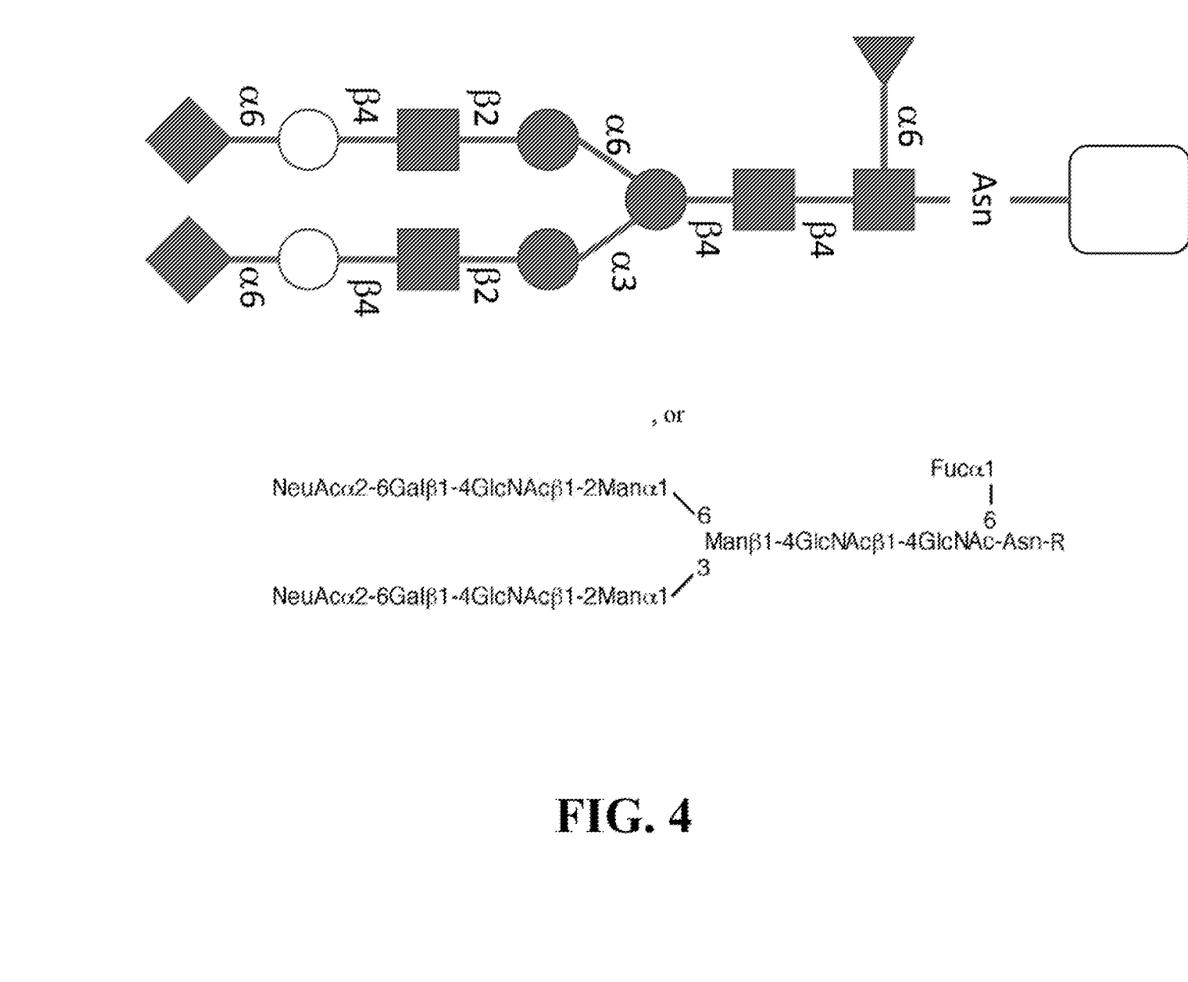
FIG. 4 illustrates an exemplary N-linked glycan bonded to an amide nitrogen of a peptide.

As shown in FIGS. 1 and 2, the exemplary glycopeptide 102 comprises an N-linked glycan 103 bonded to an amide nitrogen of an asparagine (Asn) residue of a peptide 101, as indicated in FIG. 4.

As shown above and in accordance with glycan symbol nomenclature, the exemplary glycan 103 thus comprises twelve monosaccharides (4 N-acetylglucosamine, 3 mannose, 2 galactose, 2 N-acetyleneuraminic acid, and 1 fucose) in a branched structure. Specifically, the exemplary glycan 103 structure comprises an N-acetylglucosamine (square) bonded to the Asn residue of the peptide 101, and which is bonded via glycosidic bonds to a fucose (triangle) and another N-acetylglucosamine. Bonded to the second N-acetylglucosamine is a single mannose (solid dark circle) from which branches two additional mannose, each branch containing another N-acetylglucosamine, which is bonded to a galactose (light circle), and terminating in a N-acetyleneuraminic acid (diamond). The a designations represent the linkages between the monosaccharides. Though FIGS. 1 and 2 depict this particular, exemplary N-linked glycan, it will be appreciated that the present teachings provide for the analysis of any N-linked glycan or O-linked glycan (i.e., a glycan linked to an oxygen atom in an amino acid residue, typically a serine or threonine residue). Moreover, it will be appreciated by a person skilled in the art that glycolipids can also be analyzed in accordance with various aspects of the present teachings, the glycolipids generally comprising a glycan structure bonded to the ceramide of a lipid molecule.

As noted above, in step 110 the sample portions 102b-e, each containing the glycopeptide to be analyzed, can be reacted with a different glycosidase 114b-e effective to cleave a particular glycosidic bond such that the resulting product 122b-e is the peptide itself 122b or the peptide bonded to a non-cleaved glycan portion (the cleaved glycan portion being released). By way of example, to sample portion 102b, a glycosidase 114b effective to cleave the entire glycan 103 from the peptide 101 can be added. Non-limiting examples of such glycosidases include PNGase (e.g., PNGase F, PNGase A, O-glycosidase) such that the product 122b resulting from the deglycosylation reaction in step 110 is the bare peptide 101. Likewise, fucosidase 114c can be reacted with sample portion 102c so as to cleave the fucose monosaccharide from the glycan 103 (resulting in product 122c), neuraminidase 114d can be reacted with sample portion 102d so as to cleave the two terminal N-acetyleneuraminic acids (resulting in product 122d), and galactosidase 114e can be reacted with sample portion 102e so as to cleave the glycosidic bonds between the galactoses and the N-acetylglucosamines (thereby releasing the galactose and the N-acetyleneuraminic acid and resulting in reaction product 122e). It will be appreciated by a person skilled in the art, in light of the present teachings, that the use of any one or multiple deglycosylation enzymes (e.g., endoglycosidases, exoglycosidases) can target specific glycosidic bonds within the glycopeptide, if any, such that the reactions of the sample portions 102b-e result in different reaction products from one another depending on the presence and structure of the glycan 103. By way of non-limiting example, methods and systems in accordance with the present teachings can utilize endoglycosidases (e.g., Endoglycosidase H, Endoglycosidase F, Endo-β-galactosidase) and exoglycosidases (e.g., N-acetyl-glucosaminidase, fucosidase, galactosidase, glucosidase, mannosidase, neuraminidase, and xylosidase), and mixtures thereof.

As noted above, in step 120, the glycopeptide 102a and differential products 122b-e resulting from step 110 can be reacted with differential labels 124a-e so as to uniquely label the original glycopeptide 102a, the bare peptide 122b, and a partial glycopeptide 122c-e (i.e., the reaction in step 110 partially cleaves the glycan) resulting from the various deglycosylation reactions (i.e., forming labeled reaction products 132a-e). Though step 120 is depicted in FIG. 1 as being a separate step that occurs after the deglycosylation reactions in step 110, it will be appreciated by a person skilled in the art that the differential labeling reactions can occur before, during, or after the deglycosylation reactions in step 110 in accordance with the present teachings. By way of non-limiting example, upon separating the sample into sample portions 102a-e, the various sample portions 102a-e can be separately labeled prior to the deglycosylation reactions, where the differential labels 124a-e remain associated with the glycopeptide 102a or cleaved glycopeptides 122b-e following the deglycosylation reactions. Alternatively, the labeling reaction can occur simultaneously with the deglycosylation reactions (e.g., by being added to the sample well concurrent with the glycosidase, if any).

Isobaric or isomeric labels are commonly utilized in mass spectrometric analysis in order to determine the relative or absolute quantity of an analyte in a plurality of different samples. For example, in a typical multiplexed workflow, multiple samples containing one or more analytes of interest are differentially reacted with labeling reagents having a unique reporter ion. The labeled analytes of the multiple samples are then mixed and subject to mass spectrometric analysis. By comparing the relative amounts of the reporter ions (e.g., the area or height of the various reporter ion peaks) that are detected in the second (MS/MS) mass analysis for a selected, labeled analyte observed in a first (MS) mass analysis, the relative amounts of the selected analyte in each of the plurality of original samples can then be calculated. This process can be repeated for all of the differentially-labeled analytes observed in the first mass analysis such that the relative amount of the analytes in each of the plurality of original samples can be determined. In accordance with various aspects of the present teachings, however, the unique differential labeling reagents can instead be used to encode the glycopeptide or cleaved glycopeptides of the sample portions such that the product resulting from a particular deglycosylation reaction can be identified. That is, the products from an identical sample 102 reacted with a particular deglycosylation enzyme can be differentially labeled in step 120 and then mixed in step 130 such that when the sample mixture is subsequently analyzed (e.g., via LC-MS/MS), the unique labeling reagents (e.g., reporter ions) can be used to identify the particular reaction from which the detected glycopeptide or cleaved glycopeptide resulted. In this way, the various reaction products in the mixture are determined in a multiplex fashion, with the analysis providing information that relates back to the reaction of the sample with the various glycosidases. It will be appreciated that any known or hereafter developed differential labeling reagent modified in accordance with the present teachings can be used. In various embodiments, the labeling reagents 124a-e can comprise isobaric and/or isomeric compositions that include a unique reporter ion that can be independently determined, for example in MS/MS analysis. By way of non-limiting example, the isobaric and/or isomeric labeling reagents can be those disclosed in WO2004/070352, incorporated by reference for any and all purposes. The isobaric and/or isomeric labeling reagents can be those disclosed in U.S. Pat. Nos. 7,195,751 and 7,799,576, the teachings of which are herein incorporated by reference in their entireties. The isobaric and/or isomeric labeling reagents can be polymer-based labeling reagents such as those described in WO02/14867 or U.S. Pat. No. 6,824,981, the teachings of which are herein incorporated by reference in its entirety. The labeling reagents can be those isobaric or isomeric labeling reagents disclosed in WO01/68664, which is also incorporated herein by reference for all purposes. Sets of isobaric labeling reagents are commercially available from SCIEX and sold as iTRAQ™ labeling reagents (e.g., iTRAQ reagents 114, 115, 116, 117, 118, etc.), all by way of non-limiting example.

As noted above, after mixing the differentially labeled products in step 130, the mixture can then be subjected to LC-MS/MS, e.g., via a single injection onto a liquid chromatography column (e.g., LC column 142) coupled to a tandem mass spectrometer 152 having the ability to select and fragment ions according to their mass-to-charge (m/z) ratio, and then record the resulting fragment (e.g., daughter) ion spectra. More specifically, daughter fragment ion spectra can be generated by subjecting selected ions to dissociative energy levels (e.g. by collision-induced dissociation (CID)). For example, ions corresponding to labeled peptides of a particular m/z ratio can be selected from a first mass analysis, fragmented and reanalyzed in a second (MS/MS) mass analysis. Representative instruments that can perform such tandem mass analysis include, but are not limited to, magnetic four-sector, tandem time-of-flight, triple quadrupole, ion-trap, and hybrid quadrupole time-of-flight (Q-ToF) mass spectrometers, all by way of non-limiting example. Moreover, it will be appreciated that these types of mass spectrometers may be used in conjunction with a variety of ionization sources that can in some aspects, be effective to ionize the analytes contained within the eluate received from the LC column 142. Generally there is no limitation on the type of mass spectrometer that can be used so long as it is possible to obtain a first mass analysis, select and fragment ions from the first mass analysis and then analyze the result of said fragmentation.

With reference now to FIG. 2, the mass spectrometric analysis of the exemplary mixture from step 130 will now be described with reference to the depicted mass spectra observed in the first mass analysis (MS) at various elution times (i.e., $t = t_{132a-e}$) of the mixture of labeled reaction products, with the exemplary glycosidases and labeling reagents added to each of the sample portions as follows: no glycosidase is added to the sample fraction 102a and is labeled with labeling reagent 124a (iTRAQ 114) so as to form labeled glycopeptide 132a; sample fraction 102b is reacted with glycosidase 114b (PNGase F) with the reaction products 122b being labeled with labeling reagent 124b (iTRAQ115) to form labeled peptide 132b; sample fraction 102c is reacted with glycosidase 114c (fucosidase) with the reaction products 122c being labeled with labeling reagent 124c (iTRAQ116) to form labeled cleaved glycopeptide 132c; sample fraction 102d is reacted with glycosidase 114d (neuraminidase) with the reaction products 122d being labeled with labeling reagent 124d (iTRAQ117) to form labeled cleaved glycopeptide 132d; and sample fraction 102e is reacted with glycosidase 114e (galactosidase) with the reaction products 122e being labeled with labeling reagent 124e (iTRAQ118) to form labeled cleaved glycopeptide 132e.

Because of differential binding properties of the different reaction products 132a-e with the LC column 142, it will be appreciated that different labeled reaction products 132a-e tend to elute at different elution times (i.e., $t=t_{132a-e}$), with each of the mass spectra in FIG. 2 representing a first MS analysis (e.g., the mass spectra of precursor ions in a survey scan in Q1). Under a tandem MS/MS regime, the precursor ions detected in the first MS analysis would then be further analyzed (e.g., subject to CID) in a second (MS/MS) analysis such that the reporter ion can be fragmented from the labeled reaction product 132a-e, with the reporter ion indicating the particular reaction and sample portion 102a-e that produced the reaction product observed in the precursor MS spectra. That is, as shown in the first mass spectra of FIG. 2, the solid, red peak (A) indicates the elution and detection of a first analyte species 132a at a first elution time (at $t=t_{132a}$), with the MS/MS analysis producing the signature of the dissociated reporter ion of iTRAQ 114 at 114 m/z (the peak is labeled red for demonstrative purposes), thereby confirming that the solid peak (A) in the precursor MS spectra corresponds to the m/z of the sample portion 102a with the labeling reagent 124a. Similarly, at a second elution time (at $t=t_{132b}$), the solid, orange peak (B) (i.e., from the second MS survey scan of FIG. 2) would indicate the m/z of the bare peptide 101 labeled with iTRAQ 115 (i.e., based on the presence of the signature reporter ion at 115 m/z in the product ion MS/MS spectra at that elution time). At a third elution time (at $t=t_{132c}$), for example, the solid, yellow peak (C) (i.e., from the third MS survey scan of FIG. 2) would indicate the m/z of the labeled reaction product 132c labeled with iTRAQ 116 (i.e., based on the presence of the signature reporter ion at 116 m/z in the product ion MS/MS spectra at that elution time). Similarly, the solid, green peak (D) would indicate the m/z of the labeled reaction product 132d and the solid, purple peak (E) would indicate the m/z of the labeled reaction product 132e at their respective elution times (at $t=t_{132d}$ and at $t=t_{132e}$, respectively).

It will thus be appreciated that the reactivity of the sample portion 102b-e with the particular glycosidase 114b-e could thus be confirmed through the detection, for example, of the signature of the particular reporter ion associated with each reaction (B)-(E) at the different elution times. By way of example, if the 114 m/z reporter ion and 116 m/z reporter ion both were present at a given elution time and at a given m/z, it could be deduced that the reaction product labeled with iTRAQ 116 had the same elution time as that of the glycopeptide labeled with iTRAQ 114 and that the particular glycosidase used in the reaction with iTRAQ 116 was not effective to cleave any glycosidic bonds (i.e., that the glycan in the original glycopeptide lacked a particular monosaccharide linkage).

In addition, it should be appreciated in light of the present teachings that the difference of the detected m/z in the MS survey scans at different elution times can indicate the changes in m/z of the labeled products at the different elution times. By way of non-limiting example, because the reaction product 132a exhibits a m/z of A (corresponding to the mass of the labeled, whole glycopeptide 102) while the reaction product 132b exhibits a m/z of B (corresponding to the mass of the bare peptide 101 and the labeling reagent 124b), the mass of the glycan 103 and/or peptide 101 can be deduced. Similarly, it should be appreciated that, based on the changes between the peak of the m/z of the first spectra (i.e., at A) and the peak of the m/z of the third spectra (i.e., at C), it can be determined that the glycosidase 114c (fucosidase) resulted in the reduction of the m/z by a value of (A-C) (i.e., the mass of the cleaved glycan portion), thereby indicating that the cleaved glycan portion was a single fucose molecule based on this reduction (i.e., the difference between the cleaved glycopeptide and the whole glycopeptide). It would be similarly apparent based on differences between the first and the fourth and fifth MS spectra that the deglycosylation reaction with glycosidase 114d (neuraminidase) results in the cleavage from the glycan of a mass corresponding to the loss of 2 N-acetylneuraminic acids, while the deglycosylation reaction with glycosidase 114e (galactosidase) results in the cleavage from the glycan of a mass corresponding to the loss of 2 galactose and two N-acetylneuraminic acid, thereby indicating that N-acetylneuraminic acids are bonded to one or more of the galactose molecules. A person skilled in the art will further appreciate that in addition to the identity of the reaction of the sample portion 102a-e, the second, product MS/MS scan can provide additional information regarding the dissociation products such as information as to the identity and/or structure of a portion of the glycan.

In some aspects of the present teachings, information from the various MS (or MS/MS spectra) can be combined so as to generate a signature representative of the particular deglycosylation reactions to which the glycopeptide is subject. By way of example, as shown in the bottom exemplary mass spectra of FIG. 2, the peaks of the products of the glycosylation reactions can be combined into a signature or barcode across the range of deglycosylation reactions to which the glycopeptide is subject. By performing a database search of the information generated by the array of the differentially labeled products (e.g., by comparing the signature of the array to the signature of known glycan structures subject to the same reactions), the glycan structure can be positively identified, or can be used to eliminate possible glycan structures from further consideration (e.g., narrow the candidate glycans). By way of example, with reference now to FIG. 3, exemplary MS spectra are depicted for exposing a different glycopeptide to the same glycosidases 114b-e and labeling reagents 124a-e used to generate the mass spectra of FIG. 2, thereby resulting in the exemplary labeled reaction products 232a-e and mass spectra depicted in FIG. 3.

Figure 3:
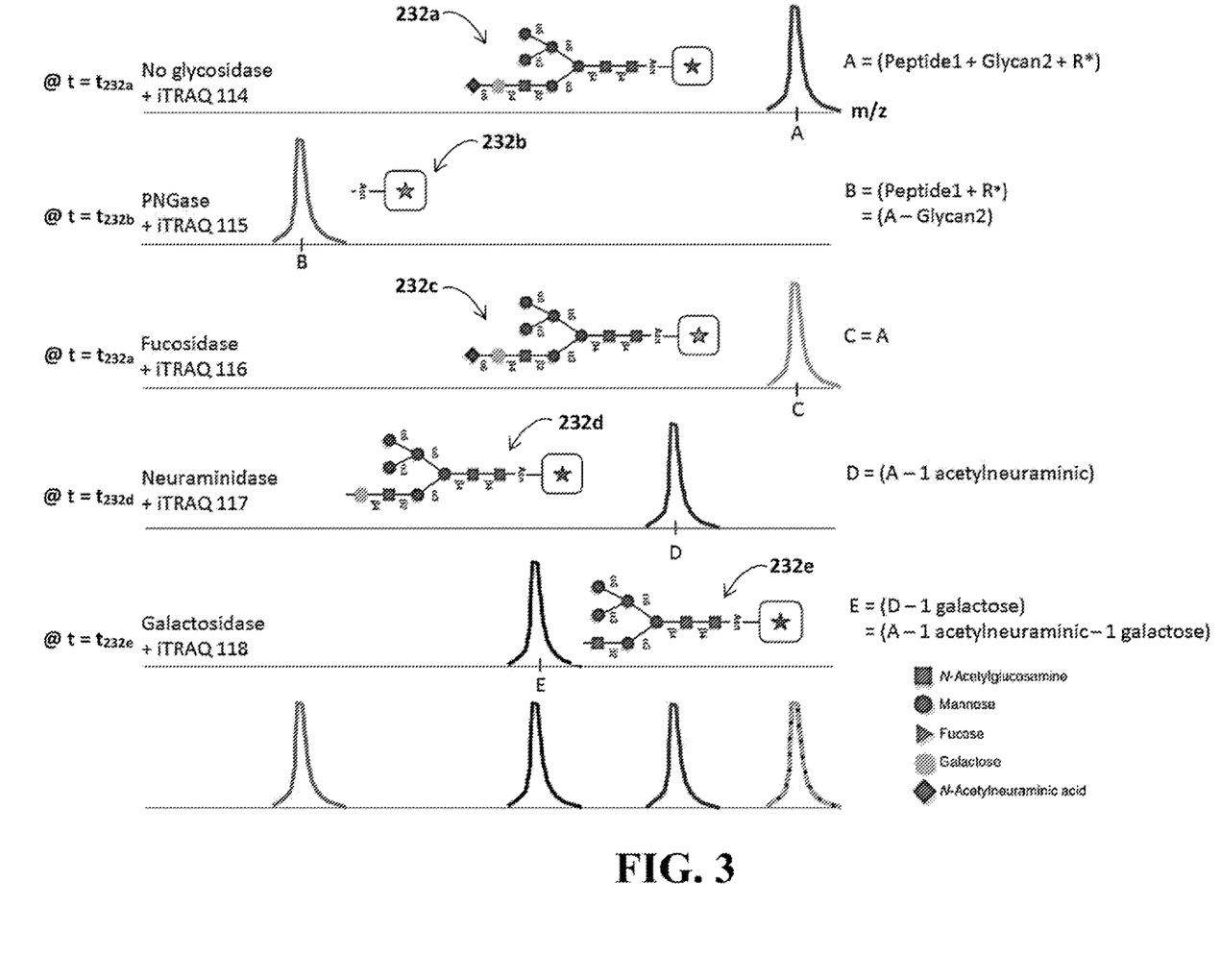
FIG. 3 illustrates exemplary mass spectra resulting from a different glycopeptide subject to the multiple deglycosylation reactions of FIG. 2.

First, as noted above, it would be expected that the reaction product 232a and 232c would both elute at the same retention time (i.e., at $t=t_{232a}$) and produce a MS product signal at an identical m/z, thereby indicating that the exposure of the reaction product to fucosidase did not remove an fucose molecules from the glycan in reaction product 232c (and thus indicating the absence of fucose).

Second, it will be appreciated by a person skilled in the art that the exposure of the various sample portions of the second exemplary glycan (whether associated with the same peptide of FIGS. 1 and 2 or a different peptide) can generate a different deglycosylation signature when subject to the same array of glycosidases. For example, it is apparent from FIG. 3 that the exemplary glycopeptide of FIG. 3 does not contain any fucose molecules as discussed above. It would be similarly apparent based on differences between the first and the fourth and fifth MS spectra that the deglycosylation reaction with neuraminidase results in the cleavage from the glycan of a mass corresponding to the loss of 1 N-acetylneuraminic acid unit, while the deglycosylation reaction with galactosidase results in the cleavage from the glycan of a mass corresponding to the loss of 1 galactose and 1 N-acetylneuraminic acid, thereby indicating that N-acetylneuraminic acid is bonded to the cleaved galactose molecule.

Thus, by exposing different glycopeptides (e.g., the same peptide with different glycans, different peptides with different glycans) to the same array of deglycosylation reactions and differential labeling, signature mass spectra resulting from the array of reactions (e.g., the bottom mass spectra of each of FIGS. 2 and 3) can be compared to one another and/or a database of known glycan structures to demonstrate differences in and/or identify possible candidates for the respective glycan structures of the glycopeptides subject to the analysis. In accordance with various aspects of the present teachings, such a method of subjecting a sample containing a glycopeptide to multiple deglycosylation reactions (e.g., each containing one or more glycosidases) can thus be automated (e.g., with a liquid transfer robot, autosampler, etc.) to detect the glycan structure based on the results of the array of the reactions.

Though the exemplary mass spectra of FIGS. 2 and 3 are depicted using a pure sample of the glycopeptide of interest, methods and systems can also be used with samples containing more than one glycopeptide. Because the MS and MS/MS spectra can become increasingly complicated with the presence of additional peptides and it can be difficult to determine which peak in the MS or MS/MS spectra came from which deglycosylation reaction, methods and systems in accordance with various aspects of the present teachings can additionally provide for the identification of the bare peptide from which the cleaved glycopeptide originated at any given elution time of the cleaved glycopeptide. As shown in FIG. 1, for example, the system can include a split fluid flow path between the outlet of the LC 142 and the inlet or ion source of the mass spectrometer 152 such that a portion of the eluate could be exposed to a glycosidase 146 during transit. For example, in some aspects, the additional glycosidase can be effective to cleave the entire glycan or the remaining cleaved glycan portion from a fraction of the eluted reaction products 132a-e such that the labeled bare peptide 101 and the labeled reaction product 132a-e would be simultaneously analyzed by the mass spectrometer (e.g., the elution time would be the same due to on-line post-column exposure to PNGase). Though a glycopeptide typically exhibits only glycan fragments in the MS/MS, thereby making it difficult to determine which peptide the glycan was attached (e.g., in a sample containing a plurality of peptides or glycopeptides), the co-analysis of the peptide and the glycopeptide makes it easier to identify the peptide and the mass of the glycan that was attached to it. For example, as shown in dotted line in each of the mass spectra of FIG. 2, the mass of the labeled, bare peptide would appear in the MS (and its fragments in the MS/MS) at each elution time of the particular reaction products 132a-e associated with the peptide. In this manner, analysis of the resulting mass spectra can be simplified in view of the positive identification of the peptide from which the particular glycan fragments originated.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

The section headings used herein are for organizational purposes only and are not to be construed as limiting. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

What is claimed is:

1. A method of analyzing a sample, comprising:
separately reacting portions of a sample with a plurality of glycosidases each of which is effective to cleave a different glycosidic bond, the sample containing a plurality of a glycopeptide of interest comprising a glycan bonded to a peptide;
differentially labeling products of each reaction between the glycopeptide and the glycosidase;
mixing the differentially labeled products to form a mixture;
performing liquid chromatography-mass spectrometry on the mixture of differentially labeled products;
determining if a cleaved glycan portion resulted from the reaction of the glycopeptide with each of the plurality of glycosidases;
at least partially determining a structure of the glycan based on the determination of whether a cleaved glycan portion resulted from the reaction of the glycopeptide with each of the plurality of glycosidases; and
comparing a mass of non-cleaved glycan portions remaining bonded to the peptide after each separate reaction with known glycan structures to at least partially determine the structure of the glycan.

2. A method of analyzing a sample, comprising:
separately reacting portions of a sample with a plurality of glycosidases each of which is effective to cleave a different glycosidic bond, the sample containing a plurality of a glycopeptide of interest comprising a glycan bonded to a peptide;
differentially labeling products of each reaction between the glycopeptide and the glycosidase;
mixing the differentially labeled products to form a mixture; and
performing liquid chromatography-mass spectrometry on the mixture of differentially labeled products; and
wherein performing liquid chromatography-mass spectrometry on the mixture further comprises transferring an eluate from a liquid chromatograph to a mass spectrometer such that a portion of the eluate is reacted with a glycosidase during transfer so as to cleave an asparagine-linked glycan from a fraction of the differentially labeled glycopeptide products present in the eluate, and producing a mass spectra from the mass spectrometer, and
wherein at any given elution time of the differentially labeled glycopeptide products, the mass spectra exhibits a peak corresponding to a mass of the glycopeptide and a peak corresponding to a mass of the peptide.

3. The method of claim 2, wherein the glycosidase reacted with the eluate comprises PNGase.

4. The method of claim 3, wherein one of the plurality of glycosidases separately reacted with portions of the sample comprises PNGase.

* * * * *